US00PP19307P3

(12) United States Plant Patent

Zaiger et al.

(10) Patent No.: US PP19,307 P3

(45) Date of Patent: Oct. 7, 2008

(54) CHERRY TREE NAMED 'ROSIE RAINER'

(50) Latin Name: *Prunus avium*
Varietal Denomination: Rosie Rainer

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 111 days.

(21) Appl. No.: 11/645,272

(22) Filed: Dec. 26, 2006

(65) Prior Publication Data

US 2008/0155722 P1 Jun. 26, 2008

(51) Int. Cl.
*A01H 5/00* (2006.01)

(52) U.S. Cl. ..... Plt./181

(58) Field of Classification Search ..... Plt./181
See application file for complete search history.

(56) References Cited

U.S. PATENT DOCUMENTS

PP5,478 P * 5/1985 Anderson et al. ..... Plt./181
PP9,783 P * 1/1997 Zaiger et al. ..... Plt./181
PP10,578 P * 9/1998 Hurlbut ..... Plt./181

* cited by examiner

*Primary Examiner*—Wendy C. Haas

(57) ABSTRACT

A new and distinct variety of cherry tree (*Prunus avium*). The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous upright growth.
2. Heavy and regular production of large size fruit.
3. Fruit with an attractive red blush over yellow-white skin.
4. Fruit with good flavor and eating quality.
5. The ability of the fruit to remain firm on the tree 6 to 7 days past maturity (shipping ripe).
6. Firm fruit with good handling and shipping qualities.

1 Drawing Sheet

Botanical classification: *Prunus avium.*
Variety denomination: 'Rosie Rainer'.

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Bing' Cherry (non-patented) and 'Earlisweet' Cherry (U.S. Plant Pat. No. 9,783).

ORIGIN OF THE VARIETY

The new and distinct variety of cherry tree (*Prunus avium*) was originated by us in our experimental orchard located near Modesto, Calif. as an open pollinated seedling from our proprietary cherry selection with field identification number '181LB359'. The proprietary cherry '181LB359' originated from the crosses of the following cherry parents, 'Bing' Cherry (non-patented) and 'Earlisweet' Cherry (U.S. Plant Pat. No. 9,783). A large number of these open pollinated seedlings were budded on older trees of 'Mahaleb' Rootstock (non-patented) to induce earlier fruit production, one budded seedling exhibited desirable fruit and tree growth characteristics and was selected in 1997 for additional asexual propagation and commercialization.

ASEXUAL REPRODUCTION OF THE VARIETY

Additional asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of cherry tree is of large size, vigorous upright growth and a regular and productive bearer of large size fruit with good flavor and eating quality. The fruit is further characterized by having an attractive red blush over yellowish-white skin and firm flesh that has the ability to hold firm on the tree 6 to 7 days past maturity (shipping ripe). In comparison to one of its parents, 'Earlisweet' Cherry (U.S. Plant Pat. No. 9,783), the fruit of the new variety has highly blushed, yellow skin instead of red and is approximately 10 days later in maturity. In comparison to its other parent 'Bing' Cherry (non-patented) the fruit of the new variety is approximately 8 days earlier in maturity.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of cherry tree, its flowers, foliage and fruit, as based on observations of 7 year old specimens grown near Modesto, Calif., with color in accordance with Munsell Book of Color.

Tree:

*Size.*—Large. Usually pruned to 3 to 3.5 meters in height and width for economical harvesting of fruit.

*Vigor.*—Moderately vigorous. Tree growth of 1.5 to 1.75 meters in height the first growing season. Varies with type of soil, cultural practices and climatic conditions.

*Form.*—Upright. Usually pruned to vase shape.

*Branching habit.*—Upright crotch angle approximately 45°, increases with heavy crop load.

*Productivity.*—Productive. Produces adequate fruit set annually.

*Bearer.*—Regular, adequate fruit set for 4 consecutive years. Amount of fruit set varies with number of pollinator trees per acre, climatic conditions and cultural conditions.

*Fertility.*—Self-sterile, pollinator required.

*Density.*—Medium dense. Pruned to vase shape to allow sunlight and air movement to center of tree to enhance fruit color and health of fruit spurs.

*Hardiness.*—Hardy in all stone fruit growing areas of California. Tree grown in USDA Hardiness Zone 9. Winter chilling requirement is approximately 850 hours at or below 45° F.

Trunk:

*Size.*—Large. Measured 38.1 cm at 35.6 cm from the ground on a 7 year old tree.

*Stocky.*—Medium stocky.

*Texture.*—Medium rough, roughness increases with age.

*Color.*—Varies from 7.5YR 2/2 to 7.5YR 6/2.

Branches:

*Size.*—Medium. Average circumference 17.5 cm measured 1.5 meters above ground.

*Surface texture.*—New growth smooth. Old growth medium rough, becomes rougher with age.

*Lenticels.*—Average number 20 in a 25.8 sq cm surface area of branch. Size — average length 4.36 mm, average width 1.54 mm. Color varies from 5YR 5/8 to 7.5YR 5/10.

*Color.*—New growth varies from 5GY 6/8 to 5GY 5/8. Old growth varies from 10R 3/2 to 2.5YR 3/2, varies with age of growth.

Leaves:

*Size.*—Large. Average length 167.1 mm. Average width 67.6 mm.

*Form.*—Lanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and pinnate venation, glabrous. Lower surface smooth except for small ridges created by midrib and pinnate venation, glabrous.

*Petiole.*—Average length 42.8 mm. Average width 2.3 mm. Color varies from 2.5GY 5/6 to 7.5R 2/4 where exposed to sunlight. Longitudinal groove, very shallow. Surface — glabrous.

*Glands.*—Reniform. Size — large. Average length 2.9 mm. Average width 2.0 mm. Average number 2, varies from 1 to 3. Located primarily on the upper portion of the petiole. Color varies from 7.5R 3/8 to 7.5R 2/8.

*Color.*—Upper surface varies from 5GY 4/8 to 5GY 3/6. Lower surface varies from 5GY 4/4 to 5GY 4/6. Midvein color varies from 10Y 7/6 to 2.5GY 7/6.

Flower buds:

*Size.*—Medium. Average length 15.4 mm. Average diameter 8.6 mm.

*Hardiness.*—Hardy with respect to California winters.

*Form.*—Conical, becoming elongated before opening.

*Pedicel.*—Average length 15.1 mm. Average width 1.1 mm. Color varies from 5GY 5/6 to 5GY 5/8.

*Color.*—N 9.5/ (white).

*Number of buds per spur.*—Average 17, varies from 15 to 27.

Flowers:

*Blooming period.*—Date of First Bloom Mar. 8, 2005. Date of Petal Fall Mar. 15, 2005, varies slightly with climatic conditions.

*Size.*—Medium. Average height 17.6 mm. Average diameter 27.7 mm.

*Petals.*—Number 5, alternately arranged to sepals. Size — medium. Average length 14.8 mm. Average width 14.0 mm. Orbicular, narrows at point of attachment. Margin sinuate. Color N 9.5/ (white).

*Sepals.*—Number 5, alternately arranged to petals. Size — small to medium. Average length 5.9 mm. Average width 4.0 mm. Ovate, margin entire. Upper and lower surface glabrous. Color — upper surface varies from 5GY 6/8 to 5GY 5/8. Lower surface varies from 5GY 6/10 to 5GY 5/8.

*Stamens.*—Average number 38. Average filament length 11.1 mm. Filament color N 9.5/ (white). Anther color varies from 5Y 8.5/8 to 5Y 8/6.

*Pollen.*—Present, pollinator required, not self fruitful. Color varies from 2.5Y 7/10 to 5Y 7/10.

*Pistil.*—Normally 1. Surface — glabrous. Average length 13.7 mm. Position of stigma even in height with the anthers. Color varies from 2.5GY 8/6 to 2.5GY 7/8.

*Fragrance.*—Slight fragrance.

*Color.*—N 9.5/ (white).

*Number flowers per flower bud.*—Average 5, varies from 5 to 7.

*Pedicel.*—Average length 20.3 mm. Average width 1.2 mm. Color varies from 5GY 5/6 to 5GY 4/8.

Fruit:

*Maturity when described.*—Firm ripe.

*Date of first picking.*—May 10, 2005.

*Date of last picking.*—May 17, 2005, varies slightly with climatic conditions.

*Size.*—Large. Average diameter axially 26.5 mm. Average transversely in suture plane 26.6 mm. Average weight 12.8 grams, varies slightly with fertility of the soil, cultural practices and climatic conditions.

*Form.*—Globose to slightly oblate.

*Suture.*—Shallow, relatively smooth, extends from base to apex.

*Ventral surface.*—Nearly rounded.

*Apex.*—Rounded to slight depression.

*Base.*—Retuse.

*Cavity.*—Rounded. Average depth 1.5 mm. Average diameter 5.5 mm.

Stem:

*Size.*—Large. Average length 45.5 mm. Average diameter 1.7 mm.

*Color.*—Varies from 5GY 5/6 to 5GY 4/8.

Flesh:

*Ripens.*—Relatively even.

*Texture.*—Firm.

*Fibers.*—Few, small and tender.

*Aroma.*—Moderate.

*Amydgalin.*—Undetected.

*Eating quality.*—Good.

*Flavor.*—Good. Good balance between sugar and acid.

*Juice.*—Moderate amount, enhances flavor.

*Brix.*—Average Brix 15.3°, varies slightly with amount of fruit per tree and climatic conditions.

*Color.*—Varies from 5Y 9/2 to 5Y 9/4. Pit cavity varies from 2.5Y 8/4 to 2.5Y 8/6.

Skin:

*Thickness.*—Medium.

*Surface.*—Smooth.

*Bloom.*—Wanting.

*Tendency to crack.*—None during dry weather. Slight tendency to crack during wet weather, varies with stage of fruit maturity.

*Color.*—Ground color varies from 5Y 8.5/4 to 5Y 8/4. Where the fruit is exposed to sunlight a blush develops which color varies from 5R 4/12 to 7.5R 3/12.

*Tenacity.*—Tenacious to flesh.

*Astringency.*—None.

Stone:

*Type.*—Semi freestone, slight adherence of flesh along ventral edge.

*Size.*—Average length 11.4 mm. Average width 10.5 mm. Average thickness 8.3 mm.

*Form.*—Obovoid.

*Base.*—Flat to slightly rounded.

*Apex.*—Rounded to slight apical point. Length 0.3 mm.

*Surface.*—Smooth with slight ridges along each side of the suture.

*Sides.*—Varies from equal to unequal. Some stones having one side extending a greater distance from the suture plane.

*Ridges.*—Two very small narrow ridges running along each side of the suture.

*Tendency to split.*—None.

*Color.*—Varies from 10YR 6/4 to 10YR 5/6 when dry.

Kernal:

*Form.*—Ovate.

*Taste.*—Bitter.

*Viability.*—Viable, complete embryo development.

*Size.*—Average length 7.8 mm. Average width 6.0 mm. Average depth 5.0 mm.

*Skin.*—Color varies from 5Y 9/4 to 7.5Y 9/4 when dry.

Use: Dessert. Market, local and long distance.

Keeping quality: Good, held firm in storage 2 weeks at 38° to 42° F. without shriveling, internal breakdown of flesh or appreciable loss of eating quality.

Shipping quality: Good, minimal bruising or scarring in packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of cherry tree, substantially as illustrated and described, characterized by its large size, vigorous upright growth and a regular and productive bearer of large size fruit with firm flesh that has the ability to remain firm on the tree for 6 to 7 days past maturity, the fruit is further characterized by having an attractive red blush over yellow-white skin, with good flavor and eating quality, and in comparison to its parent 'Earlisweet' Cherry (U.S. Plant Pat. No. 9,783), the new variety has yellowish-white skin instead of red and ripens approximately 10 days later.

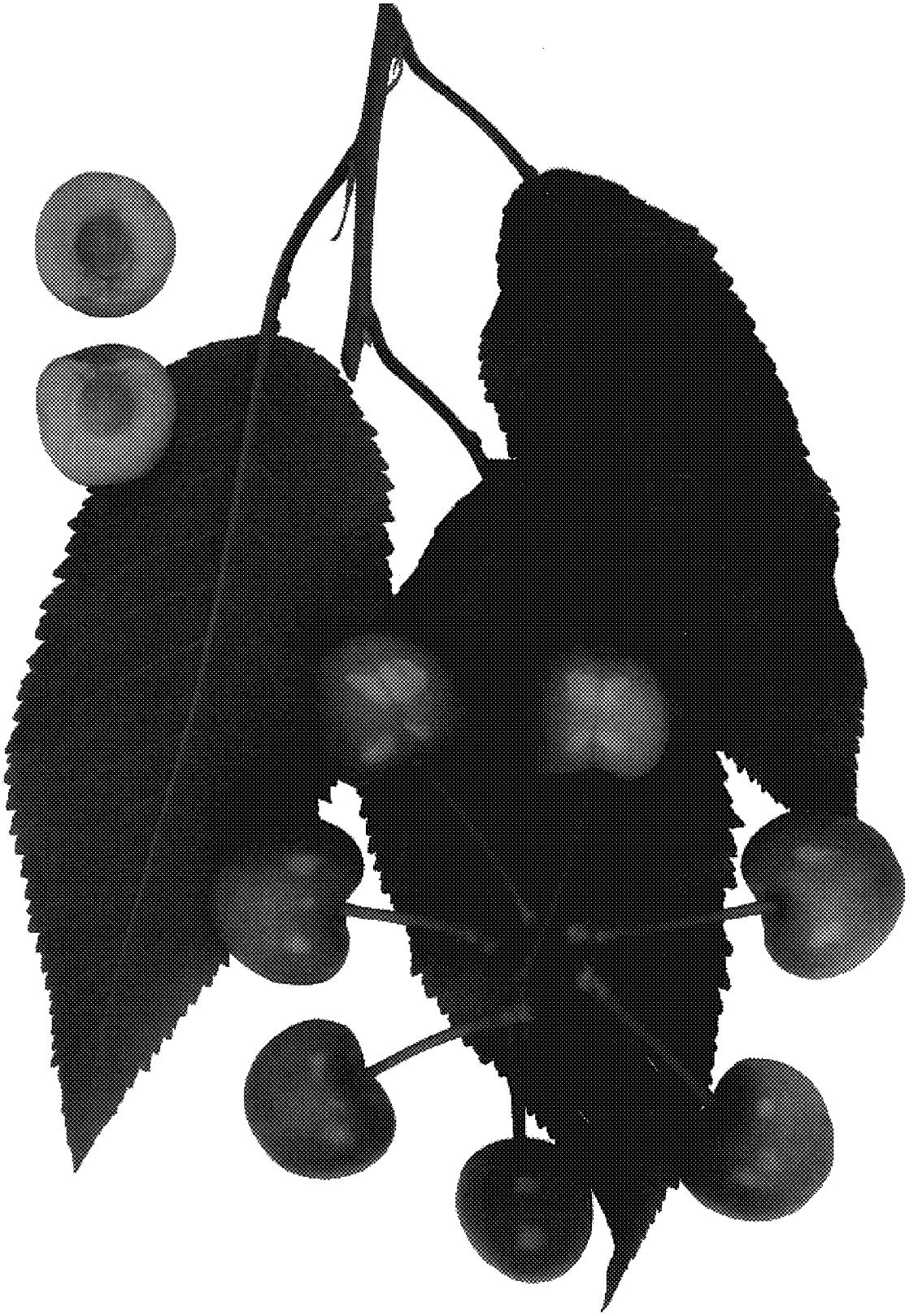

* * * * *